(12) United States Patent
Urano et al.

(10) Patent No.: US 11,661,622 B2
(45) Date of Patent: *May 30, 2023

(54) BLOOD ANALYSIS METHOD AND BLOOD TEST KIT

(71) Applicant: FUJIFILM Corporation, Tokyo (JP)

(72) Inventors: Hikaru Urano, Kanagawa (JP); Haruyasu Nakatsugawa, Kanagawa (JP); Tatsuya Ishizaka, Kanagawa (JP); Shinya Sugimoto, Tokyo (JP); Isao Yonekubo, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 1008 days.

This patent is subject to a terminal disclaimer.

(21) Appl. No.: 16/452,553

(22) Filed: Jun. 26, 2019

(65) Prior Publication Data

US 2019/0316175 A1  Oct. 17, 2019

Related U.S. Application Data

(63) Continuation of application No. PCT/JP2017/047203, filed on Dec. 28, 2017.

(30) Foreign Application Priority Data

Dec. 28, 2016  (JP) .............................. JP2016-255674

(51) Int. Cl.
*G01N 1/38* (2006.01)
*C12Q 1/52* (2006.01)
(Continued)

(52) U.S. Cl.
CPC ................. *C12Q 1/52* (2013.01); *B01L 3/52* (2013.01); *G01N 1/38* (2013.01); *G01N 33/491* (2013.01); *G01N 2333/91188* (2013.01)

(58) Field of Classification Search
CPC ........... C12Q 1/52; B01L 3/52; G01N 33/491; G01N 2333/118; G01N 1/38; G01N 2333/91188; G01N 33/96; G01N 33/48
(Continued)

(56) References Cited

U.S. PATENT DOCUMENTS 6,471,868 B1    10/2002  Ito et al.
2001/0055784 A1  12/2001  Noda et al.
(Continued)

FOREIGN PATENT DOCUMENTS

CN        1421700      6/2003
CN        101539582    9/2009
(Continued)

OTHER PUBLICATIONS

"Office Action of China Counterpart Application," with English translation thereof, dated Dec. 11, 2019, p. 1-p. 14.
(Continued)

*Primary Examiner* — Christine T Mui
(74) *Attorney, Agent, or Firm* — JCIPRNET

(57) ABSTRACT

An object of the present invention is to provide a blood analysis method and a blood test kit, which are for performing quantitative analysis of components by precisely obtaining a dilution factor. According to the present invention, provided is a blood analysis method including a step of diluting a collected blood sample with a diluent solution; a step of determining a dilution factor by using a normal value of a normal component which is homeostatically present in blood; and a step of analyzing a concentration of a target component in the blood sample, in which the blood analysis method uses a member selected from the group consisting of a first storing instrument for storing a diluent solution, a separation instrument for separating and recovering blood plasma from the blood sample diluted with the diluent
(Continued)

solution, a holding instrument for holding the separation instrument, a second storing instrument for storing the recovered blood plasma, and a sealing instrument for keeping the stored blood plasma within the second storing instrument, in which the diluent solution defines an amount of the normal component which is derived from the diluent solution and/or the members and may be contained in the diluent solution, and in which a volume of the blood sample is 50 µL or less, and a dilution factor of a blood plasma component in the blood sample is 14 times or more.

9 Claims, 1 Drawing Sheet

(51) Int. Cl.
*B01L 3/00* (2006.01)
*G01N 33/49* (2006.01)
*G01N 33/48* (2006.01)

(58) Field of Classification Search
USPC .......................................................... 435/16
See application file for complete search history.

(56) References Cited

U.S. PATENT DOCUMENTS

| | | | |
|---|---|---|---|
| 2002/0153316 A1 | 10/2002 | Nanba et al. | |
| 2003/0036202 A1 | 2/2003 | Teodorcyzk et al. | |
| 2003/0175167 A1 | 9/2003 | Takanori et al. | |
| 2004/0141888 A1 | 7/2004 | Nanba et al. | |
| 2004/0219624 A1 | 11/2004 | Teodorcyzk et al. | |
| 2009/0230291 A1 | 9/2009 | Sakazume et al. | |
| 2011/0020195 A1* | 1/2011 | Luotola ............ | A61B 5/150351 206/569 |
| 2016/0011150 A1* | 1/2016 | Onuma ............ | G01N 27/44747 204/451 |
| 2017/0205433 A1 | 7/2017 | Osawa et al. | |

FOREIGN PATENT DOCUMENTS

| | | | | |
|---|---|---|---|---|
| EP | 3321675 | 5/2018 | | |
| EP | 3321676 | 5/2018 | | |
| EP | 3321677 | 5/2018 | | |
| EP | 3321678 | 5/2018 | | |
| JP | H11347017 | 12/1999 | | |
| JP | 2000254461 | 9/2000 | | |
| JP | 2001330603 | 11/2001 | | |
| JP | 2003161729 | 6/2003 | | |
| JP | 2003270239 | 9/2003 | | |
| JP | 3597827 | 12/2004 | | |
| JP | 2009109196 | 5/2009 | | |
| JP | 2009122082 | 6/2009 | | |
| JP | 2014-141829 | * | 7/2014 | ........... G01N 27/447 |
| JP | 2015105936 | 6/2015 | | |
| JP | 2016102806 | 6/2016 | | |
| JP | 2016118565 | 6/2016 | | |
| WO | 03005039 | 1/2003 | | |

OTHER PUBLICATIONS

Osawa, Susumu et al., "Revolution of medical services at home using a small amount of blood collected from the fingertip", Journal of Clinical Laboratory Medicine,vol. 59, No. 5,May 15, 2015, pp. 397-404.

Osawa, Susumu et al., "Development of an assay for measuring biochemical parameters in 65-µL fingertip blood samples collected at home", 68th AACC Annual Scientific Meeting Abstracts, Aug. 3, 2016, pp. 1-1.

"International Search Report (Form PCT/ISA/210) of PCT/JP2017/047203," dated Apr. 3, 2018, with English translation thereof, pp. 1-5.

"Written Opinion of the International Searching Authority (Form PCT/ISA/237) of PCT/JP2017/047203," dated Apr. 3, 2018, with English translation thereof, pp. 1-10.

"Office Action of China Counterpart Application" with partial English translation thereof, dated Sep. 14, 2020, p. 1-p. 5.

"Search Report of Europe Counterpart Application", dated Sep. 25, 2019, p. 1-p. 6.

"Office Action of Japan Counterpart Application", dated Apr. 7, 2020, with English translation thereof, p. 1-p. 8.

Susumu Osawa, et al., "Delivery Method of the Test Results and the Clinical Laboratory Technology and Offer of the Clinical Laboratory Technology to be Possible at Home," Japanese Journal of Clinical Laboratory Automation, vol. 41, 2016, pp. 154-160.

"Office Action of China Counterpart Application", dated May 13, 2020, with English translation thereof, pp. 1-15.

Office Action of European Counterpart Application, dated Feb. 11, 2022, pp. 1-8.

* cited by examiner

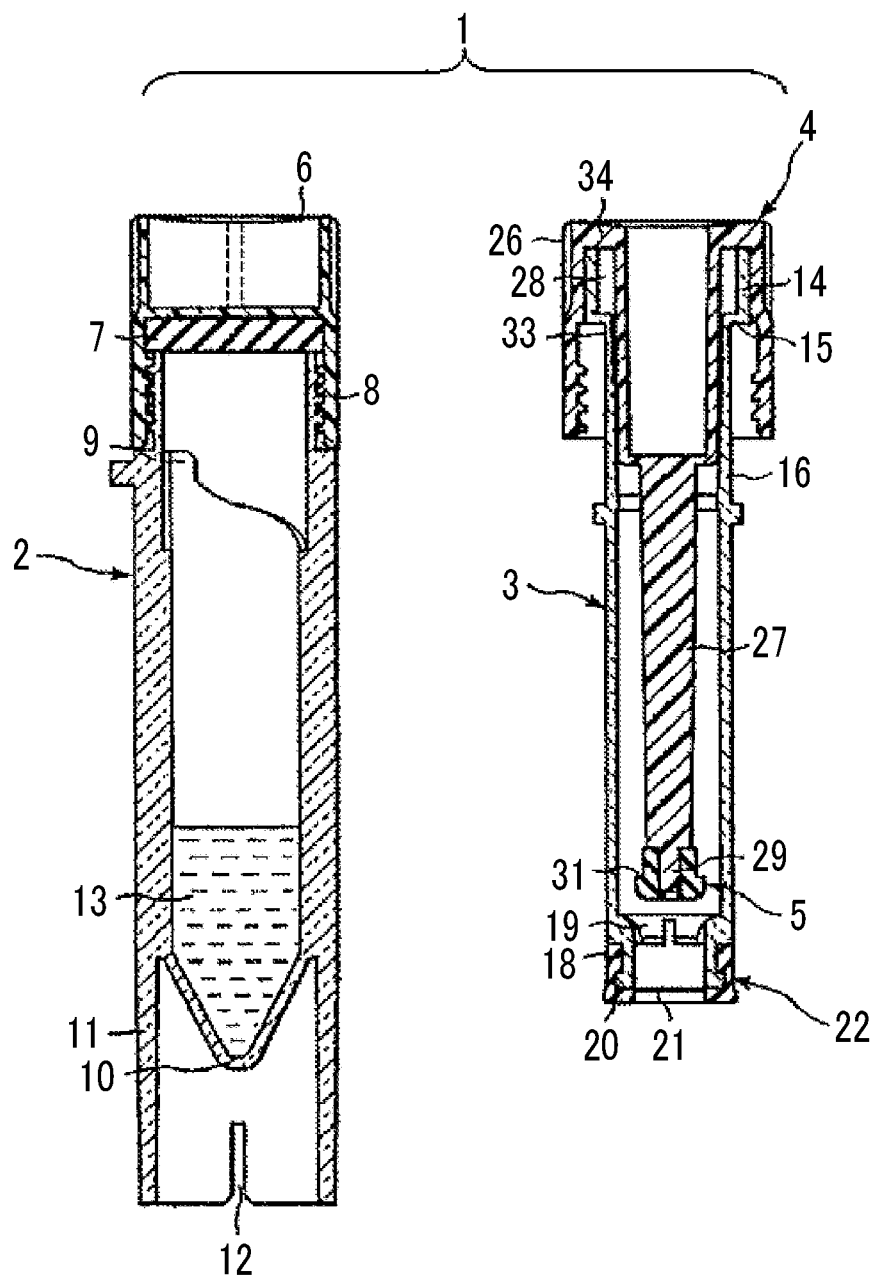

BLOOD ANALYSIS METHOD AND BLOOD TEST KIT

CROSS-REFERENCE TO RELATED APPLICATIONS

This application is a Continuation of PCT International Application No. PCT/JP2017/047203 filed on Dec. 28, 2017, which claims priority under 35 U.S.C § 119(a) to Japanese Patent Application No. 2016-255674 filed on Dec. 28, 2016. Each of the above application(s) is hereby expressly incorporated by reference, in its entirety, into the present application.

BACKGROUND OF THE INVENTION

1. Field of the Invention

The present invention relates to a blood analysis method and a blood test kit, which are for analyzing a target component in a small volume of a blood sample.

2. Description of the Related Art

As blood collection, in general, there are general blood collection in which a qualified person such as a doctor collects blood from the vein using a syringe, and self-blood collection in which a subject to be tested pricks his finger and the like using a blood collection needle so as to collect blood.

The blood collected by the general blood collection is transported to a medical institution or a test institution in a state of being sealed in a blood collection container, and tests are performed therein. In a case where the blood is transported without separating blood cells and blood plasma, tests are performed after a medical institution or a test institution separates the blood into blood cells and blood plasma with a centrifuge. In addition, in the self-blood collection which is performed by a subject to be tested, the collected blood is separated into blood cells and blood plasma by a separation membrane, the blood is transported to a test lab in this separated state, and then tests are performed therein.

JP2003-161729A discloses a method for testing a blood sample collected by self-blood collection. JP2003-161729A specifically discloses a method for quantitatively determining a component to be quantitatively determined in a biological specimen, the method including 1) step of preparing a specimen for quantitation composed of a biological specimen with an unknown volume which contains a component to be quantitatively determined, which is collected without quantitatively determining a volume thereof, and an aqueous solution with a certain volume which contains a certain amount of an indicator substance; 2) step of obtaining a dilution factor (a) of the biological specimen from a concentration ($C_1$) of the indicator substance in the aqueous solution with a certain volume which contains a certain amount of the indicator substance, and a concentration ($C_2$) of the indicator substance in the specimen for quantitation; 3) step of obtaining a concentration (Y) of the component to be quantitatively determined in the specimen for quantitation; and 4) step of determining the component to be quantitatively determined in the biological specimen from the dilution factor (a) of the biological specimen obtained in 2), and the concentration (Y) of the substance to be quantitatively determined in the specimen for quantitation obtained in 3).

JP2001-330603A discloses a quantitative analysis method in which an amount of a target component to be analyzed in a sample is measured; an amount of a normal component other than the target component to be analyzed, which is originally and homeostatically present in the sample, is measured; a volume of the sample is determined from the amount of this normal component and a known concentration of the normal component in the sample; and a concentration of the target component to be analyzed in the sample is determined from the volume of this sample and the amount of the target component to be analyzed.

In addition, JP2009-122082A discloses that, using an instrument for blood dilution and quantitation, a small volume of blood is collected from a human or an animal, and after dilution or without dilution, a certain volume thereof is supplied to another instrument or container or is directly supplied to a reagent. Furthermore, JP2009-109196A discloses a method for quantitatively determining a concentration of a component to be quantitatively determined in a biological specimen by utilizing an absorbance of an indicator substance in an aqueous solution for dilution.

Meanwhile, in a case where a subject to be tested collects a blood sample, the blood is collected by using a lancet equipped with a small blade and is used for quantitatively determining a concentration of any component in the blood. In generally, it is required to collect 100 µL, or more of a blood sample.

SUMMARY OF THE INVENTION

In the method disclosed in JP2003-161729A, it is required that a ratio of a diluent solution to a blood sample volume be set high in a case of a small volume of a blood sample. However, in this case, a change rate in a volume of a diluent solution before and after diluting the blood sample becomes very small, and thus a change rate in a concentration of an internal standard substance becomes small. Therefore, there is a problem of a decrease in level of repeatability and reproducibility with respect to measurement values.

JP2001-330603A discloses that about 100 µL of whole blood of a healthy subject is added dropwise to a porous membrane, blood cells are separated to develop blood serum, and thereafter, a solution obtained by adding 150 µL of a physiologically isotonic phosphate-buffered saline (PBS, pH of 7.4) thereto is centrifuged, and a supernatant thus obtained is analyzed as an analytical specimen, but does not disclose collection of blood of less than 100 µL.

In the method of JP2009-122082A, 10 µL of a blood volume is precisely collected with a micropipette so as to be analyzed, but in a case where the blood is collected by a patient who lacks experience in blood collection, it is difficult to precisely collect a certain volume thereof, resulting in errors in measurement values in a case where tests are performed with collected blood volumes including errors.

The measurement method disclosed in JP2009-109196A is the measurement with a dilution factor of about 10, but in a case where a dilution factor is further raised to sufficiently secure a volume of diluted blood, there is the same problem as in JP2003-161729A of a decrease in level of repeatability and reproducibility with respect to measurement values.

As described above, a blood analysis method in which a high level of repeatability and reproducibility is achieved with respect to measurement values in a case of using a small volume of a blood sample, is desired. The inventors of the present invention have examined a method in which an external standard substance is used in consideration of using an internal standard substance, which has been proposed in the related art, being not sufficient for performing, with high accuracies, a blood analysis method in which a high level of repeatability and reproducibility is achieved with respect to measurement values in a blood sample of 50 µL, or less.

An object of the present invention is to provide a blood analysis method and a blood test kit, which are for quantitatively analyzing a component by precisely obtaining a dilution factor, at accuracy not described in the related arts of, for example, JP2003-161729A and JP2001-330603A by defining a concentration of a normal component homeostatically present in blood, which is eluted from a member of the blood test kit into a buffer solution in a method for analyzing a concentration of a target component in a blood sample by using a normal component homeostatically present in blood as a method for quantitatively analyzing a component by diluting 50 µL or less of blood, which is a small volume, with a buffer solution.

As a result of intensive studies to achieve the above-described object, the inventors of the present invention have found that the object can be achieved by a configuration in which a volume of a blood sample is 50 µL or less, a dilution factor of a blood plasma component in the blood sample is 14 times or more, and as a diluent solution, a diluent solution defining an amount of a normal component which is derived from the diluent solution and/or members of a blood test kit and may be contained in the diluent solution is used, in the blood analysis method in which a collected blood sample is diluted with a diluent solution, a dilution factor is determined by using a normal value of a normal component which is homeostatically present in blood, and a concentration of a target component in the blood sample is analyzed; and therefore have completed the present invention. That is, according to the present invention, the following inventions are provided.

(1) A blood analysis method, comprising:
a step of diluting a collected blood sample with a diluent solution;
a step of determining a dilution factor by using a normal value of a normal component which is homeostatically present in blood; and
a step of analyzing a concentration of a target component in the blood sample,
in which the blood analysis method uses a member selected from the group consisting of a first storing instrument for storing a diluent solution, a separation instrument for separating and recovering blood plasma from the blood sample diluted with the diluent solution, a holding instrument for holding the separation instrument, a second storing instrument for storing the recovered blood plasma, and a sealing instrument for keeping the stored blood plasma within the second storing instrument,
the diluent solution defines an amount of the normal component which is derived from the diluent solution and/or the members and may be contained in the diluent solution, and
a volume of the blood sample is 50 µL or less, and a dilution factor of a blood plasma component in the blood sample is 14 times or more.

(2) The blood analysis method according to (1), in which an amount of the normal component which is derived from the members of the blood test kit and may be contained in the diluent solution is 0.35 mmol/L or less with respect to the diluent solution.

(3) The blood analysis method according to (1) or (2), in which the normal component which is homeostatically present in blood is sodium ions or chloride ions.

(4) The blood analysis method according to any one of (1) to (3), in which the normal component which is homeostatically present in blood is sodium ions or chloride ions, and at least one kind of another normal component.

(5) The blood analysis method according to (4), in which the at least one kind of the other normal component is a normal component selected from total protein or albumins.

(6) The blood analysis method according to (4) or (5), further comprising a step of verifying analysis of a concentration of the target component from a dilution factor obtained by using a normal value of the at least one kind of the other normal component.

(7) The blood analysis method according to any one of (1) to (6), in which the diluent solution does not contain the normal component which is homeostatically present in blood.

(8) The blood analysis method according to any one of (1) to (7), in which the diluent solution is a buffer solution having a buffering action within a pH range of pH 6.5 to pH 8.0.

(9) The blood analysis method according to any one of (1) to (8), in which the diluent solution contains an amino alcohol compound selected from the group consisting of 2-amino-2-methyl-1-propanol, 2-ethylaminoethanol, N-methyl-D-glucamine, diethanolamine, and triethanolamine, and contains a buffering agent selected from the group consisting of 2-[4-(2-hydroxyethyl)-1-piperazinyl] ethanesulfonic acid also called HEPES, N-tris(hydroxymethyl)methyl-2-aminoethanesulfonic acid also called TES, 3-morpholinopropanesulfonic acid also called MOPS, and N,N-bis(2-hydroxyethyl)-2-aminoethanesulfonic acid also called BES.

(10) A blood test kit used in the blood analysis method according to any one of (1) to (9), the blood test kit comprising: a first storing instrument for storing a diluent solution; a separation instrument for separating and recovering blood plasma from a blood sample diluted with the diluent solution; a holding instrument for holding the separation instrument; a second storing instrument for storing the recovered blood plasma; and a sealing instrument for keeping the stored blood plasma within the second storing instrument.

According to a blood analysis method and a blood test kit of the present invention, a concentration of a target component in a blood sample can be analyzed with high accuracies using a normal component which is homeostatically present in blood.

BRIEF DESCRIPTION OF THE DRAWINGS

FIG. 1 is a cross sectional diagram of a blood test kit according to an embodiment of the present invention.

DESCRIPTION OF THE PREFERRED EMBODIMENTS

Hereinafter, the present invention will be described in detail. A range indicated by X to Y includes values of an upper limit X and a lower limit Y. A normal component which is homeostatically present in blood may be referred to as an external standard substance or an external standard. In addition, a normal component which is not present in blood may be referred to as an internal standard substance or an internal standard.

In a case of performing a blood test, the blood is collected by inserting a blood collection needle into the vein of a subject to be tested, or the blood is collected by a method in which the skin such as a fingertip is pricked, and the blood flowing out of the skin is collected. Both methods are invasive actions that damage the skin, which is accompanied by patient's pain. Therefore, a method in which the blood is collected, in a manner of relieving patient's pain by suppressing invasiveness as much as possible to reduce the damage on the skin, and the blood is analyzed is desired from many patients. In this case, reducing the damage on the skin reduces the pain, but because a volume of blood collection becomes small, there is an adverse effect that the type of a target component that can be tested is limited. In a case of attempting to solve the above adverse effect by applying such an aspect to the test method of JP2003-161729A, by increasing a ratio of a volume of a diluent solution to a volume of blood collection, in the diluent solution by which the blood is diluted, a sufficient volume is secured for enabling tests of all of the target components to be analyzed, which is required to be tested. However, in a case where a volume of blood collection is small, a change rate in a volume of a diluent solution before and after diluting the blood becomes extremely small, and a change rate of a substance used as an internal standard substance also becomes extremely small. Therefore, quantitative errors at the time of weighing and measurement errors at the time of measurement become relatively large, and there is a possibility that the reliability of the test may deteriorate due to a deterioration of measurement accuracy, a decrease in the level of repeatability and reproducibility, and the like. Accordingly, for a test in which the level of reproducibility with respect to measurement values is high, it was necessary to secure a certain volume of a blood sample, and it was necessary to perform a blood collection method which is accompanied with subject's pain to some extent.

In JP2001-330603A, a blood volume of about 100 μL was collected, but in a case where a patient collects 100 μL of blood by himself, it is required that the damage on the skin such as a fingertip is increased, which leads to patient's pain, and there is a case of feeling strong pain depending on the person. In addition, there is a concern that hemostasis may be delayed as the damage would be deep. Furthermore, in JP2001-330603A, a dilution factor is measured using 0.9 mmol/L of magnesium ions, 4.65 mmol/L of calcium ions, and 7.5 g/100 mL of total protein, the values being a homeostatic central value in blood, which are the amount of homeostatic component. However, in a case where a volume of blood collected by a patient is small, a concentration of the homeostatic component in a diluent solution decreases, resulting in a measurement error that cannot be ignored in a case of measuring the homeostatic component. As a result, the error is also included in the measurement values of a dilution factor, and therefore the reliability of measurement deteriorates.

In the method of JP2009-122082A, with respect to 10 μL of a blood volume, which is a small volume, a certain volume thereof is accurately collected with a micropipette so as to be analyzed, but in a case where the blood is collected by a patient, there are many patients who lack experience in blood collection, and therefore it is difficult to accurately and constantly collect a certain volume thereof. In a case where the blood is collected by a patient, the blood is collected repeatedly, and therefore a large volume of the blood flows out of the skin, but a case where tests are performed with the collected blood volumes including errors will result in measurement values including the error.

JP2009-109196A discloses a technique for improving measurement accuracy by correcting the influence of chyle through utilization of light of two wavelengths, but the measurement is performed with a dilution factor of about 10. The method of JP2009-109196A is effective for analysis in which a volume of diluted blood is 100 μL or less, but an amount of target components to be analyzed is small, and therefore, the method cannot be applied to a test to be used for a prediction and the like of a state of the organ and a lifestyle habit by obtaining information of a plurality of target components to be analyzed. In this case, in a case where a dilution factor is further increased to sufficiently secure the volume of diluted blood, the same problem occurs as in JP2003-161729A.

The present invention has been studied in consideration of the above problems and is preferable because, even in a case where a volume of blood to be collected is set to be small so as to alleviate the burden on a patient by reducing the invasiveness when collecting the blood, it is possible to realize a dilution factor by which a high level of reproducibility is achieved when a dilution factor is made large so that a volume of a diluent solution to be analyzed is sufficiently secured; and because analysis of a target component with high accuracies is realized, and thus a normal component which is present at a high concentration in a small volume of blood is measured. In the present invention, it is preferable to use sodium ions ($Na^+$) or chloride ions ($Cl^-$) which are present at a high concentration among components homeostatically present in a blood sample. Furthermore, it is most preferable to measure sodium ions which are present in blood at a highest amount, among the above-mentioned normal components homeostatically present in blood. Regarding sodium ions, an average value represents a normal value (a median value within a reference range), and this value is 142 mmol/L accounting for 90 mole % or more of total cations in blood plasma.

In examples of these related arts, a phosphate buffered saline is used in a buffer solution for extraction because the phosphate buffered saline is excellent for stably maintaining a biological component, but the phosphate buffered saline contains sodium ions or chloride ions. For this reason, sodium ions and chloride ions cannot be used external standards, and thus calcium ions, proteins, and the like are used. Accordingly, for performing a blood test using a small volume of blood with high accuracies, use of an external standard substance for correcting a dilution factor as disclosed in the related art and use of a buffer solution containing an internal standard substance proposed in the related art were not sufficient for ensuring test accuracies.

In addition, even in a case of homeostatic substances in blood, in sodium ions for example, a distribution width of a normal value is 134 to 146 mmol/L, and therefore it is necessary to more precisely calculate a dilution factor. A decrease in accuracies of a dilution factor affects a bad influence on test accuracies, thereby making a risk of a deterioration in reliability of a test high. Particularly, in a case where even little contamination due to an external standard substance eluted from a member constituting a kit into a buffer solution is present, and in a case where a volume of blood collected changes, a degree of influence of contamination on calculation of a dilution factor varies. JP2001-330603A does not all mention about curbing such a degree of influence of the contamination due to the external standard substance eluted from the member constituting the kit into the buffer solution, on the calculation of the dilution factor.

The present invention provides a blood analysis method for analyzing a concentration of a target component by diluting, with a buffer solution, a sample having a small volume of blood collected which is less burden on patients, the method capable of obtaining a dilution factor with accuracies not described in the related art in a case where analysis of a target component is performed using an external standard homeostatically present in blood. A solution for achieving the above-described object is a diluent solution which defines an amount of the normal component which is derived from diluent solution components and/or members of a blood test kit and may be contained in the diluent solution.

There are two types of normal components which may be contained in a diluent solution, which are a component derived from a chemical substance dissolved in the diluent solution, and a component eluted from a member for correcting the blood test kit. As the former component derived from a chemical substance dissolved in the diluent solution, for example, components in which sodium is used as a counter ion, such as an anticoagulant or a buffer solution, and the like are considered in a case where sodium is used as a normal component. Examples of the latter case include components originally contained in a container for storing a buffer solution, a separation membrane for separating blood cells, filters, and the like; components remaining by being bonded to a surface in a preparation stage of these members; and the like. In the present invention, in a case where a volume of blood collected is a small volume, an amount of normal components derived from the blood and carried into the diluent solution is small, and errors that occur in a case where the above-mentioned normal components which may be contained in the diluent solution are present to some extent are relatively large. Accordingly, a diluent solution is a diluent solution defining an amount of the above-described normal components which are derived from the above-described members and may be contained in the diluent solution, and the above-described amount is preferably defined to an extremely low value. In this case, it is required that an amount of standard substances derived from chemical substances constituting a diluent solution and from a solvent be a small amount that can be negligible, and that an amount of standard substances derived from members such as a container for storing a buffer solution and a separation membrane for separating blood cells be an amount that can guarantee accuracies of blood analysis. With such a configuration, even in a case where a volume of blood collected is small and a dilution factor of blood plasma by a diluent solution is large, it is possible to precisely obtain the dilution factor of blood plasma, and it is possible to perform a blood analysis method in which a high level of repeatability and reproducibility is achieved with respect to measurement values. These are effects that cannot be predicted from the documents of the related art.

In a case where sodium homeostatically present in blood is used as a normal component, as described later, by measuring a concentration of sodium ions in a mixed solution of blood plasma and a diluent solution, a homeostatic average value of a concentration of sodium ions in blood plasma, which is 142 mmol/L, is used to calculate a dilution factor, and therefore a concentration of a target component present in separated and recovered blood plasma can be calculated. In this case, by suppressing an amount of sodium ions (an amount of sodium ions not derived from blood, that is, contamination components) in a diluent solution, which are derived from the members of the blood test kit, to about 0.05 times or less an amount of sodium ions in blood plasma, it is possible to maintain error accuracy in calculation of a dilution factor at about 5%. For example, in a case where an amount of diluent solution is 350 µL, a volume of blood collected is 30 µL, and a proportion of blood plasma components is 55%, and in a case where an amount of sodium components which are derived from the members of the kit and may be contained in the diluent solution is 0.35 mmol/L or less with respect to the diluent solution, an amount of sodium components is about 5% by mass with respect to sodium ions derived from blood plasma. Therefore, test accuracies can be maintained within a range of error accuracy of about 5%. In addition, in a case where an amount of sodium components is 0.15 mmol/L or less with respect to the diluent solution, it can be understood that test accuracies can be maintained within a range of error accuracy of about 2%. An amount of sodium components which are derived from the members of the kit and which may be contained in a diluent solution is preferably small, and is preferably 0.35 mmol/L or less, is more preferably 0.15 mmol/L or less, and even more preferably 0.10 mmol/L or less.

Blood Sample

In the present invention, a biological specimen which is a target of the blood analysis method of the embodiment of the present invention is blood, and the blood is a concept of including blood serum or blood plasma. The origin of blood is not limited to humans, and may be mammals, birds, fish, and the like which are animals other than humans (non-human animals). Examples of the animals other than humans include horses, cows, pigs, sheep, goats, dogs, cats, mice, bears, pandas, and the like. The origin of a biological specimen is preferably humans.

In the present invention, a blood sample is collected to analyze a target component in a blood sample. The blood analysis method of the present invention may be carried out by self-blood collection in which a subject collects blood by himself, or may be carried out by general blood collection in which a qualified person such as a doctor collects blood using a syringe.

As a preferred embodiment, there is a method in which a patient pricks the fingertip and the like by himself using an instrument equipped with a small blade such as a lancet, and then collects blood flowing out of the skin. It is preferable that the blood be collected in a manner of decreased invasiveness so as to alleviate the burden on a patient. It is more preferable to be able to collect the blood painlessly or with extremely little pain when collecting the blood. In this case, it is desired that a depth and a size of the wound are small, by which a volume of blood that can be collected is very small as a result. Accordingly, a volume of the blood sample used in the blood analysis method of the present invention (that is, a volume of the collected blood) is 50 µL or less, is preferably 40 µL or less, more preferably 30 µL or less, and further preferably 20 µL or less. A lower limit thereof is not particularly limited, but a volume is preferably 5 µL or more as a blood volume which is generally needed for performing blood analysis. In the present invention, even in a case of a small volume of a blood sample, it is possible to accurately perform analysis of a target component.

The blood to be collected contains blood plasma components and blood cell components, but the blood plasma components which is obtained by removing the blood cell components from the blood is diluted with a diluent solution so as to measure a concentration of a target component in the blood plasma components. The blood plasma components may be diluted with a diluent solution after separating the blood cell components from the blood in advance, or the blood cell components may be separated by using a separation membrane and the like after the collected blood is diluted with the diluent solution. However, it is preferable to separate and recover a blood plasma component-containing specimen after the collected blood sample is diluted with the diluent solution.

In a case where the blood is left alone for a long period of time in a diluted state, for example, there is a possibility that hemolysis of red blood cells occurs, which leads to the elution of substances, enzymes, and the like which are present at a high concentration in the blood cells into the blood plasma or blood serum, by which a test result is affected; or that hemoglobin components eluted from red blood cells affect the test. Therefore, it is preferable to isolate the blood plasma component-containing specimen from blood cells after the blood plasma component-containing specimen is separated from blood cells. In this case, it is possible to transport the blood plasma component-containing specimen isolated from blood cells to a test place, for example.

The method for recovering blood plasma by separating blood cells from the blood and the method for recovering a blood plasma component-containing specimen by separating blood cells from the diluted blood are not particularly limited. The blood can be separated into blood cell components and blood plasma components by collecting the blood in a blood collection tube containing an anticoagulant and then centrifuging the blood, or blood cell components can be separated from the blood by applying pressure on the blood components to allow the components to pass through a separation membrane such as filtration membrane, and then trapping the blood cell components with the separation membrane. In this case, an anticoagulant may be used. The step of recovering the blood plasma components is preferably a step of using the separation membrane, among the above steps. In addition, in order to ensure accuracy of measurement, it is preferable to physically isolate the blood plasma from the solution portion excluding blood cell components in blood. In this case, specifically, it is possible to use a biological specimen-separation instrument having a backflow prevention means described in JP2003-270239A, and the like.

Dilution of Blood Sample

In the present invention, the collected blood sample is diluted with a diluent solution.

In a case of testing a specific organ or a specific disease such as liver function, renal function, metabolism, and the like as a blood test, analysis of a plurality of target components is generally performed at the same time in order to perform a prediction and the like of a state of the organ, a lifestyle habit, and the like by obtaining information of the plurality of target components to be measured which are specific to the organ or the disease. For example, in order to test the state of a liver, generally, a concentration of various components in the blood such as ALT (alanine transaminase), AST (aspartate aminotransferase), γ-GTP (γ-glutamyl transpeptidase), ALP (alkaline phosphatase), total bilirubin, total protein, and albumins is measured. As above, in order to measure the plurality of target components from one blood sample, a certain volume of diluted blood is required in a case of considering a possibility of measuring again. Accordingly, regarding a diluent solution for diluting the collected blood, it is required that a certain volume of the diluent solution is used. Regardless of a volume of the collected blood, as a volume of the diluent solution to be used for measuring a plurality of target components, 250 μL or more is preferable, 300 μL or more is more preferable, 350 μL or more is further preferable, and 400 μL or more is most preferable. An upper limit of a volume of the diluent solution is not particularly limited, but generally, 1000 μL or less is preferable so that a dilution factor effective for measurement is realized.

Dilution Factor

An occupancy rate of blood plasma components in the blood of a subject to be tested who is a patient is about 55% in terms of a volume ratio, but the ratio varies depending on changes in salt intake of the subject, and the like, or varies for each subject. Therefore, in the present invention, a dilution factor is determined by using a normal value of the normal component which is homeostatically present in blood, and a concentration of a target component in a blood sample is analyzed by using the determined dilution factor. As a method for determining a dilution factor, it is possible to calculate a dilution factor (Y/X) of the blood plasma components in a blood sample from a measurement value (concentration X) of a standard substance in a diluent solution of the blood plasma, and a known concentration value (concentration Y) of a standard substance homeostatically present in blood plasma. Using this dilution factor, a measurement value (concentration Z) of a target component in a diluent solution of the blood plasma is measured, and by multiplying this measurement value by the dilution factor, it is possible to measure a concentration $[Z\times(Y/X)]$ of a target component to be analyzed actually contained in a blood sample.

Blood collection with low invasiveness is preferable for a subject to be tested such as a patient, and a diluent solution of blood is prepared from a small volume of blood sample. Meanwhile, as described above, since a certain volume of a diluent solution is required to enable analysis of a plurality of target components to be measured, a dilution factor of a blood plasma component in the blood sample is made to be large. In the present invention, in order to enable blood collection with low invasiveness, a dilution factor of a blood plasma component in collected blood is 14 or larger, preferably 17 or larger, more preferably 21 or larger, even more preferably 25 or larger, particularly preferably 30 or larger, and most preferably 40 or larger. An upper limit thereof is not particularly limited, but is 100 or less is preferable such that highly accurate measurement is possible. In a case where a dilution factor is a dilution factor of blood itself, with which blood containing blood cells is diluted with a diluent solution, a dilution factor thereof is preferably 8 or larger, more preferably 10 or larger, even more preferably 13 or larger, and most preferably 18 or larger. An upper limit thereof is not particularly limited, but is 50 or less is preferable such that highly accurate measurement is possible.

Standard Substance

As described above, in a case of using a substance that is present in a diluent solution in advance as a standard substance used for analysis of a target component in diluted blood plasma in which a dilution factor of a blood plasma component is larger, there is an adverse effect in which a concentration change of the standard substance before and after dilution is very small, and measurement errors of a dilution factor becomes large, and thus reproducibility of the measurement deteriorates. Meanwhile, in the method of the embodiment of the present invention in which a dilution factor is determined by using a normal value of a normal component homeostatically present in blood, a concentration change of a standard substance before and after dilution is large, and measurement errors become small, and thus reproducibility of the measurement is favorably maintained. Therefore, a blood analysis method becomes possible with high measurement accuracies. The normal component which is homeostatically present in blood is also called an external standard substance.

Examples of the normal component which is homeostatically present in blood include sodium ions, chloride ions, potassium ions, magnesium ions, calcium ions, total protein, albumins, and the like. As a concentration of these normal components contained in blood serum and blood plasma of a blood sample, a concentration of sodium ions is 134 to 146 mmol/L (average value: 142 mmol/L), a concentration of chloride ions is 97 to 107 mmol/L (average value: 102 mmol/L), a concentration of potassium ions is 3.2 to 4.8 mmol/L (average value: 4.0 mmol/L), a concentration of magnesium ions is 0.75 to 1.0 mmol/L (average value: 0.9 mmol/L), a concentration of calcium ions is 4.2 to 5.1 mmol/L (average value: 4.65 mmol/L), a concentration of total proteins is 6.7 to 8.3 g/100 mL (average value: 7.5 g/100 mL), and a concentration of albumins is 4.1 to 5.1 g/100 mL (average value: 4.6 g/100 mL). In order to enable blood collection with low invasiveness of a patient or a subject to be tested, it is preferable to use a normal component present at a high concentration in blood in order to perform, with high accuracies, measurement of a target component even with a small volume of blood collected. In the present invention, it is preferable to use sodium ions ($Na^+$) or chloride ions ($Cl^-$) which are present at a high concentration among components homeostatically present in a blood sample. Furthermore, it is most preferable to measure sodium ions which are present in blood at a highest amount, among the normal components. Sodium ions account for 90% or more of total cations in blood plasma.

Verification

In addition, in order to confirm whether concentration analysis of a target component to be analyzed in the blood is normally performed, it is preferable that, by using two or more different components which are homeostatically present in blood as a normal component so as to separately obtain for each of dilution factors of blood plasma components in a blood sample, whether values thereof almost match be confirmed. As a preferred embodiment, by confirming that a dilution factor obtained from a normal component homeostatically present in blood plasma, which is other than sodium ions, almost the same value as compared with a dilution factor obtained from a concentration of sodium ions, it is possible to confirm that the concentration analysis of a target component to be analyzed in the blood, which is performed using a dilution factor obtained from the measurement value of the concentration of sodium ions in a diluent solution of the blood plasma, is normally performed. Examples of the method for measuring chloride ions include the electrode method (Ion Selective Electrode: ISE) using an ion selective electrode, the enzyme method using an enzyme such as amylase, the silver nitrate titration method, and the like, and it is possible to select a method to be used appropriately depending on characteristics, sensitivity, specimen amount, and the like of a measurement specimen. A preferable embodiment of the present invention is a case in which a normal component which is homeostatically present in blood is preferably sodium ions or chloride ions, or another normal component which is homeostatically present in blood. In this case, examples of normal components which are homeostatically present in blood plasma, other than sodium ions and chloride ions, and which are used for verification, are preferably selected from total protein or albumins, and more preferably selected from total protein. Examples of methods for measuring total proteins include known methods such as a biuret method, an ultraviolet absorption method, a Bradford method, a Lowry method, a bicinchoninic acid (BCA) method, and a fluorescence method. It is possible to appropriately select a method to be used depending on characteristics, sensitivity, a specimen amount, and the like of a measurement specimen.

A concentration of sodium ions and a concentration of chloride ions can be measured by, for example, a flame photometric method, a glass-electrode method, a titration method, an ion selective electrode method, an enzyme activity method, and the like.

In the present invention, analyzing of a concentration of a target component in a blood sample includes determining a concentration of a target component (that is, quantifying a target component), determining whether a concentration of a target component is equal to or higher than a predetermined reference value or equal to or lower than a predetermined reference value, performing qualitative analysis measurement for detecting that a certain amount of concentration is contained, and the like, and an embodiment of analysis is not particularly limited.

Diluent Solution

In the present invention, it is possible that a normal component which is homeostatically present in blood (hereinafter will also be referred to as homeostatic substance) is measured after dilution with a diluent solution, and a dilution factor is determined in the above-described manner to analyze a concentration of a target component in a blood sample. A chemical substance or solvent used as a diluent solution for diluting a blood sample preferably does not contain (does not have) a "normal component homeostatically present in blood," which is used for obtaining a dilution factor. The phrase "does not contain" in the present specification means that a diluent solution "substantially does not contain" a normal component. The phrase "substantially does not contain" means that the solution does not contain a homeostatic substance used for obtaining a dilution factor at all, or even if the homeostatic substance is contained, this means a case where an ultra-small volume of concentration is contained to the extent that does not affect measurement of a homeostatic substance in a diluent solution after diluting a blood sample. In a case where sodium ions or chloride ions are used as a homeostatic substance, a chemical substance or solvent used as a diluent solution preferably and substantially does not contain sodium ions or chloride ions.

In the present invention, after a blood sample collected by a patient or subject to be tested is diluted, it is possible to transport the sample to a medical institution or a test institution so that a concentration of a target component is analyzed. In this case, a long period of time may be required in some cases from blood collection to analysis, and therefore during this time, it is preferable to prevent decomposition or denaturation of a target component of blood plasma in a diluent solution. A pH of blood is generally maintained constant at a pH of about 7.30 to 7.40 for healthy subjects. Accordingly, in order to prevent decomposition or denaturation of a target component, a diluent solution is preferably a buffer solution containing a buffering component having a buffering action within a pH range of pH 6.5 to pH 8.0, preferably pH 7.0 to pH 7.5, and even more preferably pH 7.3 to pH 7.4.

As the type of the buffer solution, there are an acetate buffer solution (Na), a phosphate buffer solution (Na), a citrate buffer solution (Na), a borate buffer solution (Na), a tartrate buffer solution (Na), a Tris (tris(hydroxymethyl) aminoethane) buffer solution (Cl), a HEPES (2-[4-(2-hydroxyethyl)-1-piperazinyl]ethanesulfonic acid) buffer solution, a phosphate buffered saline (Na), and the like. Among these, as a buffer solution around pH 7.0 to pH 8.0, a phosphate buffer solution, a Tris buffer solution, and a HEPES buffer solution are representative. However, application of a case where sodium ions or chloride ions are used as a standard substance to the present invention is not preferable because of conditions in which the phosphate buffer solution contains a sodium salt of phosphoric acid; the Tris buffer solution has a dissociation pKa (Ka is an acid dissociation constant) of 8.08, and thus is usually used in combination with hydrochloric acid for imparting buffering ability around pH 7.0 to pH 8.0; and a dissociation pKa of sulfonic acid of HEPES is 7.55, but in order to adjust buffer solution at constant ionic strength, a HEPES mixture of sodium oxide and sodium chloride is used.

As a diluent solution used in the present invention, using a buffer solution containing no sodium ions or chloride ions is preferable. It is preferable to use at least an amino alcohol compound selected from the group consisting of 2-amino-2-methyl-1-propanol (AMP), 2-ethylaminoethanol, N-methyl-D-glucamine, diethanolamine, and triethanolamine; and a buffering agent selected from the group consisting of 2-[4-(2-hydroxyethyl)-1-piperazinyl]ethanesulfonic acid (pKa=7.55) also called HEPES which is a buffering agent having a pKa around 7.4, N-tris(hydroxymethyl)methyl-2-aminoethanesulfonic acid also called TES (pKa=7.50), 3-morpholinopropanesulfonic acid also called MOPS (pKa=7.20), and N,N-bis(2-hydroxyethyl)-2-aminoethanesulfonic acid also called BES (pKa=7.15), which are Good's buffer solutions (Good's buffers). Among these, a combination of 2-amino-2-methyl-1-propanol (AMP) with HEPES, TES, MOPS, or BES is preferable, and a combination of 2-amino-2-methyl-1-propanol (AMP) with HEPES is most preferable.

For preparing the buffer solution described above, an amino alcohol may be mixed with the Good's buffer solutions at a concentration ratio of 1:2 to 2:1, preferably 1:1.5 to 1.5:1, and more preferably 1:1. A concentration of the buffer solution is not limited, but a concentration of the amino alcohol or the Good's buffer solution is 0.1 to 1000 mmol/L, preferably 1 to 500 mmol/L, and more preferably 10 to 100 mmol/L.

A chelating agent, a surfactant, an antibacterial agent, a preservative, a coenzyme, a saccharide, and the like may be contained in the buffer solution in order to keep a target component to be analyzed stable. Examples of chelating agents include a salt of ethylenediaminetetraacetic acid (EDTA), citrate, oxalate, and the like. Examples of the surfactant include a cationic surfactant, an anionic surfactant, an amphoteric surfactant, and a nonionic surfactant. Examples of the preservative include sodium azide, antibiotics, and the like. Examples of the coenzyme include pyridoxal phosphate, magnesium, zinc, and the like. Examples of the saccharide of a red blood cell-stabilizing agent include mannitol, dextrose, oligosaccharide, and the like. Particularly, by adding the antibiotics, it is possible to suppress the growth of bacteria which are partially mixed from the surface of the finger at the time of collecting blood from the finger, and stabilize the decomposition of biological components by bacteria.

In a case where whole blood is used for a blood sample, filtration of blood cell components in a diluted blood through a filter is required, and by setting osmotic pressure of the buffer solution equivalent to (285 mOsm/kg (mOsm/kg is an osmotic pressure that 1 kg of water of the solution has, and indicates millimoles of ions)) or higher than that of the blood, it is possible to prevent hemolysis of blood cells. The osmotic pressure can be adjusted to be isotonic by measurement of a target component; salts, saccharides, or buffering agents, which do not affect measurement of a normal component homeostatically present in blood; and the like.

Target Component

A target component to be analyzed in a blood sample of the present invention is not particularly limited, and any substance contained in the blood is a target. Examples thereof include biochemical test items in blood used for clinical diagnosis, markers of various diseases such as tumor markers and hepatitis markers, and the like, and include proteins, saccharides, lipids, low molecular weight compounds, and the like. In addition, not only a concentration of a substance is measured, but also an activity of a substance having an activity such as an enzyme is targeted. Measurement of each target component can be carried out by a known method. Furthermore, in a case of testing a specific organ or a specific disease such as liver function, renal function, metabolism, and the like, analysis of a plurality of target components is performed at the same time in order to perform a prediction and the like of a state of the organ, a lifestyle habit, and the like by obtaining information of the plurality of target components to be measured which are specific to the organ or the disease. For example, in order to test the state of a liver, a concentration of various components in the blood such as ALT (alanine transaminase), AST (aspartate aminotransferase), γ-GTP (γ-glutamyl transpeptidase), ALP (alkaline phosphatase), total bilirubin, total protein, and albumins is measured.

Blood Test Kit

The blood test kit of the embodiment of the present invention includes a first storing instrument for storing a diluent solution, a separation instrument for separating and recovering blood plasma from a blood sample diluted with the diluent solution, a holding instrument for holding the separation instrument, a second storing instrument for storing the recovered blood plasma, and a sealing instrument for keeping the stored blood plasma within the second storing instrument. As the example of the blood test kit of the present invention, the kit can include a diluent solution for diluting components in a blood sample, a first storing instrument in which the diluent solution is stored, a separation instrument for separating and recovering blood plasma from the blood sample diluted with the diluent solution, a holding instrument for holding the separation instrument, a second storing instrument for storing the recovered blood plasma, a sealing instrument for keeping the stored blood plasma in the second storing instrument, a needle or a lancet for pricking the skin to allow blood to flow out of the skin, a strip of bandage or a sterile swab to be put on the wound (for example, nonwoven fabrics impregnated with isopropanol (70% isopropanol and the like), ethanol, or the like), an instruction manual, and the like. As the separation instrument for recovering blood plasma components from the diluted blood sample, an aspect of the separation membrane is preferable, and a filter having fine pores capable of separating blood cell components is more preferable.

Regarding the first storing instrument and the second storing instrument, one instrument may be used as both the first storing instrument and the second storing instrument, or an embodiment in which instruments are provided separately may be used. The first storing instrument and the second storing instrument are preferably made of a transparent material such that a patient or a measurer who performs measurement of a dilution factor and analysis of a target component to be analyzed can check a diluent solution in the storing instrument, by which the blood is diluted.

As the holding instrument for holding the separation instrument, an aspect of a gasket is preferable. In addition, as the sealing instrument, in a case where the storing instrument is an instrument having a tubular shape, and the like, it is possible to use a cap capable of being used as a lid for the opening, a lid having a helical groove, a rubber closure, and the like.

With the above configuration, by imparting the function of separating blood plasma from blood cells to the container in which the blood is mixed with the diluent solution immediately after diluting the blood with the diluent solution, it is possible to eliminate the influence on the stability of the blood components and the variation of the components due to hemolysis from blood cells, and to impart the stability to the specimen after blood collection.

The blood analysis method of the embodiment of the present invention is capable of realizing a method in which a target component to be analyzed can be analyzed at high measurement accuracy even with a volume of blood collection of 50 µL or less. The blood test kit for blood analysis is preferably a kit including an instruction manual in which information that measurement can be accurately performed even with a small volume of blood collection of 50 µL or less, and the like is described for a patient.

Specific Example of Blood Test Kit

In one preferred embodiment, the blood test kit for blood analysis includes, in addition to the capillary, the diluent solution, the first storing instrument in which the diluent solution is stored (which also may be a storing instrument for storing a dilution of a blood sample), the separation instrument for separating and recovering blood plasma from a blood sample diluted with the diluent solution, the holding instrument for holding the separation instrument, the second storing instrument for storing the recovered blood plasma, and the sealing instrument for keeping the stored blood plasma in the second storing instrument. As specific examples of the instruments, it is possible to use instruments described in FIG. 1 to FIG. 13 of JP3597827B. FIG. 1 of JP3597827B is incorporated as FIG. 1 of the present application.

A blood separation instrument 1 includes a blood collection container 2 (storing instrument in which a diluent solution is stored, which may be referred to as the first storing instrument in some cases. This is a storing instrument for storing a dilution of a blood sample), a tubular body 3 capable of being to fit into the blood collection container 2 so as to be inserted (second storing instrument for storing recovered blood plasma), a cap piston 4 capable of being capped on the tubular body 3, and a sealing lid 5 (sealing instrument) provided at a lower end of the cap piston 4. Before use, an upper end opening portion of the blood collection container 2 is sealed by a cap 6 via a packing 7, as shown in FIG. 1. The storing instrument for storing a diluted blood sample of the present invention corresponds to a combination of the blood collection container 2 and the tubular body 3 in the configuration of FIG. 1. That is, the storing instrument for storing a diluted blood sample may be one or a combination of two or more thereof.

The blood collection container 2 is made of a transparent material and has a cylindrical shape. At the upper end portion thereof, a screw portion 8 is formed on the outer surface, and a locking portion 9 is protruded toward the inner surface. In addition, at a lower end portion of the blood collection container 2, a bottom portion 10 having an inverted conical shape is formed, and a cylindrical leg portion 11 is formed around the bottom portion 10. The leg portion 11 has the same outer diameter as a sample cup used at the time of an analytical test of blood, and at positions opposite to the lower end thereof, slit grooves 12 are preferably formed in a vertical direction, respectively. Furthermore, a predetermined volume, for example, 500 mm$^3$ of a diluent solution 13 may be put in the blood collection container 2 in advance, as shown in FIG. 1.

The tubular body 3 is made of a transparent material and has a cylindrical shape, and at an upper end portion thereof, an expanded diameter section 14 is formed. The expanded diameter section 14 is connected to a main body portion 16 via a thin portion 15. A reduced diameter section 18 is formed at the lower end portion of the tubular body 3, and a protruded locking portion 19 is formed on the inner surface of the reduced diameter section 18. Furthermore, at a lower end portion of the reduced diameter section 18, an outer flange portion 20 (holding instrument) is formed, a lower end opening portion of the outer flange portion 20 is covered with a filtration membrane 21 (separation instrument), and the filtration membrane 21 allows blood plasma in the blood to pass through and prevents passage of the blood cells.

A cover 22 made of silicone rubber is attached to the outer periphery of the reduced diameter section 18 (FIG. 1).

The cap piston 4 is constituted by a substantially cylindrical knob portion 26 and a mandrel portion 27 concentric with the knob portion 26 and extending downward. At an inner upper end portion of the knob portion 26, a cylindrical space 28 into which the expanded diameter section 14 of the tubular body 3 is capable of being fitted to be inserted is formed, and the knob portion is threaded in a lower portion into which a screw can screw. The mandrel portion 27 has a lower end portion 29 formed in a pin shape, and the sealing lid 5 is attachably and detachably provided on the lower end portion 29 (refer to FIG. 1). The sealing lid 5 is made of silicone rubber.

Specifically, the operation of separating and recovering blood plasma from a dilution of a blood sample is performed as below. The collected blood is added to the blood collection container 2 storing the diluent solution, and then the blood and the diluent solution are thoroughly shaken to be mixed while noting that bubbles are not generated by holding an upper portion of the blood collection container 2. Next, the tubular body 3 holding the filtration membrane 21 (for preventing solution leakage due to infiltration into a side surface of a cylinder at the time of separating blood plasma from blood cells) is inserted into the blood collection container 2 such that the filtration membrane faces downward, and the filtration membrane is slowly pushed into the bottom of the blood collection container 2 at a constant speed. At this time, the blood plasma passes through the filtration membrane of the tubular body 3 and then floats on the upper portion, and the blood cells remain on the lower portion of the blood collection container 2. Thereafter, the cap piston 4 is slowly pushed into the tubular body 3, by which mixing of the blood plasma with the blood cells due to backflow is prevented by the sealing lid 5.

A method for separating blood by the instruments described above is described in detail in paragraphs 0023 to 0026 and FIG. 12 and FIG. 13 of JP3597827B, the contents of which are incorporated in the present specification.

Elution from Members of Kit

In the kit of the present invention, an amount of a normal component homeostatically present in blood, which is derived from the member of the blood kit and may be contained in the diluent solution is defined. It is possible to obtain an amount which may be contained in the diluent solution by actually exposing a target member to the diluent solution not containing a normal component having an appropriate amount for a certain time, and then measuring an amount of a normal component which is derived from the member and becomes to be contained in the diluent solution. An amount of a normal component homeostatically present in blood, which is derived from the member of the blood kit and may be contained in the diluent solution is preferably small, and a lower limit value thereof is not particularly limited.

In the blood test kit, a fiber lot is generally used for an aspirator for collecting blood, and a sodium salt of EDTA is used as an anticoagulant in this fiber lot. In addition, a glass filter is used as an instrument for separating and recovering blood plasma, in which a small amount of sodium ions such as soda glass and sodium carbonate is contained. Soda glass is obtained by mixing and melting quartz sand ($SiO_2$), sodium carbonate ($Na_2CO_3$), and calcium carbonate ($CaCO_3$). In a case where a material of the gasket for holding the glass filter and the sealing instrument for keeping the stored blood plasma in the second storing instrument is made of rubber, there is a case where a small amount of sodium ions is contained as a residue from NaOH cleaning for deproteinization, a release agent (mixture of sodium nitrate, sodium nitrite, and the like) which is used for molding, and the like. In a member which is a plastic (resin) molded product, a small amount of Na may be contained on the surface thereof in some cases. This is because, as metal elements in the release agent used for resin molding, sodium is contained together with tin, zinc, calcium, and the like.

It is presumed that these are mixed into the diluent solution as sodium ions derived from members of the kit. According to the examination by the inventors of the present invention, by setting an amount of a normal component homeostatically present in blood (preferably sodium ions or chloride ions), which is derived from the kit and may be actually contained in the diluent solution, to be sufficiently small, specifically, by curbing an amount of sodium ions derived from blood plasma mixed with a diluent solution to about 3% or less, it is possible to maintain an error accuracy of about 3% in the calculation of a dilution factor. As described above, for example, in a case where an amount of diluent solution is 350 μL, a volume of blood collected is 30 μL, and a proportion of blood plasma components is 55%, and in a case where an amount of sodium components which are derived from the members of the kit and may be contained in the diluent solution is 0.35 mmol/L or less with respect to the diluent solution, an amount of sodium components is about 5% by mass with respect to sodium ions derived from blood plasma. Therefore, test accuracies can be maintained within a range of error accuracy of about 5%. As described above, an amount of sodium components derived from members of the kit is preferably small, and is preferably 0.35 mmol/L or less, is more preferably 0.15 mmol/L or less, and even more preferably 0.10 mmol/L or less.

Means for defining an amount of sodium ions which are derived from members of the kit and are mixed into a diluent solution to a sufficiently small amount, can be obtained by washing members of the kit with water such as pure water, which does not contain sodium ions in advance, preferably a plurality of times. In this case, in a case where each of a plurality of members is washed by the same method with pure water, actual final blood is diluted, and a diluent solution is held until a target component in the blood is finally analyzed, it is preferable to confirm, in advance, whether, in all of the plurality of members, sodium ions are sufficiently washed away, and a concentration of sodium ions eluted into the diluent solution is lowered to the extent that measurement accuracies can be maintained.

EXAMPLES

Hereinafter, reference examples, examples, and comparative examples of the present invention will be explained.

Reference Example 1

1. Washing Member and Preparation of Diluent Solution

DEMECAL blood test kit (Leisure, Inc.) was used. In this case, blood test kits were prepared in which a bottle that is a member of the blood test kit (first storing instrument for storing a diluent solution), a filter (separation instrument for separating and recovering blood plasma from a blood sample diluted with the diluent solution), and a gasket (holding instrument for holding the separation instrument) were subjected to no washing, to washing with distilled water one time, or to washing pure water (electric conductivity 1 μS/cm) three times. Thereafter, 350 μL of Diluent Solution-1 prepared as below was added to the bottle, the filter held by the gasket was pushed into the bottle to filter the diluent solution, and an amount of sodium ions in the solution passed through the filter was measured. The washing was performed in a manner of showering the member with water.

Composition of Diluent Solution

Diluent Solution-1 was prepared with the following composition. As osmotic pressure, a value measured by using OSMOATAT OM-6040 (manufactured by ARKRAY, Inc.) is shown. A unit of the osmotic pressure is an osmotic pressure that 1 kg of water of a solution has, and indicates millimoles of ions.

| | |
|---|---|
| HEPES | 50 mmol/L |
| 2-amino-2-methyl-1-propanol (AMP) | 50 mmol/L |
| D-Mannitol | 284 mmol/L |
| Lithium chloride | 1 mmol/L |
| EDTA-2K | 0.8 mmol/L |
| Pyridoxal phosphate (PALP) | 0.05 mmol/L |
| Thiabendazole | 0.0001% by mass |
| Amikacin sulfate | 0.0003% by mass |
| Kanamycin sulfate | 0.0005% by mass |
| Meropenem trihydrate | 0.0005% by mass |
| Osmotic pressure | 355 mOsm/kg |
| pH 7.4 | |

2. Measurement of Concentration of Sodium

The measurement of a concentration of sodium in the diluent solution prepared in 1. was carried out by the enzyme activity method utilizing that β-galactosidase is activated by sodium, which is that each concentration of sodium in the diluent solution and β-galactosidase activity are in a proportional relationship. Specifically, after diluting Diluent Solution-1 five times, which was filtered as above with purified water not containing sodium ions, 3 μL was weighed, 52 μL of a first reagent prepared as described below was added thereto, and then heated at 37° C. for 5 minutes. 26 μL of a second reagent prepared as described below was added thereto, and the change in absorbance was obtained by measuring an absorbance during 1 minute at a main wavelength of 410 nm and a complementary wavelength of 658 nm by using JCA-BM6050-type automatic biochemistry analyzer (manufactured by JEOL Ltd.). The concentration of sodium was measured from a calibration curve prepared in advance.

Preparation of Reagent for Measuring Sodium

A reagent for measuring sodium having the following composition was prepared.

| First reagent | |
|---|---|
| HEPES/LiOH (pH 8.0) | 100 mmol/L |
| D-Mannitol | 60 mmol/L |
| N-acetylcysteine | 30 mmol/L |
| Magnesium sulfate | 1.52 mmol/L |
| β-galactosidase | 1.1 kU/L |
| TRITON X-100 | 0.05% by mass |
| Second reagent | |
| HEPES/LiOH (pH 8.0) | 100 mmol/L |
| o-Nitrophenyl-β-D-galactopyranoside | 15 mmol/L |

Ten sets of blood test kits washed by washing methods shown in Table 1 were prepared, and an average value of an amount of Na ions eluted into each of Diluent Solutions-1 filtered, and coefficient of variation (CV) (%) which is a measure of the variation were obtained. The results are shown in Table 1.

TABLE 1

| Washing method | Number of washing | Diluent Solution-1 (μL) | Concentration of Na ions eluted into diluent solution (mmol/L) | CV of concentration of Na ions eluted into diluent solution (%) |
|---|---|---|---|---|
| Washing with distilled water | 1 | 350 | 2.0 | 4.3 |
| Washing with pure water | 3 | 350 | 0.12 | 3.1 |
| No washing | 0 | 350 | 6.0 | 5.2 |

Reference Example 2

1. Preparation of Diluent Solution with which Small Volume of Blood Sample is Diluted After informed consent was obtained from a volunteer patient, about 10 mL of blood collected from the vein by a syringe was obtained in a blood collection tube. From this collected blood, 80 μL, 60 μL, 40 μL, 30 μL, and 20 μL were precisely weighed 20 times respectively with a micropipette, and each was mixed with 350 μL of Diluent Solution-1 which is the same as the diluent solution prepared in Reference Example 1. It was confirmed in advance that there was almost no sodium eluted from the syringe and the micropipette. As a blood test kit including Diluent Solution-1, a blood test kit of which members were washed with distilled water and washed with pure water as shown in Table 2 in the same manner as in Reference Example 1 was used. The obtained mixed solution of blood and a diluent solution was allowed to pass through a filter to separate blood cell components, and therefore diluted blood plasma was obtained. Using this obtained diluted blood plasma as a specimen, a concentration of sodium ions was measured in the same manner as in Reference Example 1.

A dilution factor (Y/X) of each diluent solution was obtained from a concentration of sodium ions (X) in the diluent solution obtained as above, and a normal value (Y: 142 mmol/L) of a concentration of sodium ions in blood plasma of the blood. An average value of the dilution factors, and coefficient of variation (CV) (%) which is a coefficient of variation of the dilution factor of 10 specimens prepared with respect to each of the collected blood (80 μL, 60 μL, 40 μL, 30 μL, and 20 μL) were obtained. The results are shown in Table 2.

TABLE 2

| Volume of blood collected (μL) | Volume of Diluent Solution-1 (μL) | Dilution factor (average value of 10 times of measurement) | CV of dilution factor (%) (10 times of measurement) | Washing | Number of washing | Notes |
|---|---|---|---|---|---|---|
| 80 | 350 | 8.1 | 3.7 | Washing with distilled water | 2 | Comparative Level 1 |
| 80 | 350 | 9.0 | 3.3 | Washing with pure water | 5 | Comparative Level 2 |
| 60 | 350 | 9.9 | 3.8 | Washing with distilled water | 2 | Comparative Level 3 |
| 60 | 350 | 11.3 | 3.5 | Washing with pure water | 5 | Comparative Level 4 |
| 40 | 350 | 14.2 | 4.5 | Washing with distilled water | 2 | Comparative Level 5 |
| 40 | 350 | 17.1 | 3.9 | Washing with pure water | 5 | Reference Level 1 |
| 30 | 350 | 17.4 | 4.7 | Washing with distilled water | 2 | Comparative Level 6 |
| 30 | 350 | 22.6 | 4.3 | Washing with pure water | 5 | Reference Level 2 |
| 20 | 350 | 25.3 | 5.3 | Washing with distilled water | 2 | Comparative Level 7 |
| 20 | 350 | 34.2 | 4.7 | Washing with pure water | 5 | Reference Level 3 |

Measurement of Lithium Ions in Diluent Solution

Next, lithium ions, in the diluent solution, of blood plasma obtained by allowing the diluent solution, and the mixed solution of blood and the diluent solution in the blood test kit washed with pure water to pass through the filter was measured by a chelate colorimetric method (halogenated porphyrin chelating method: perfluoro-5,10,15,20-tetraphenyl-21H,23H-porphyrin). Specifically, after diluting diluted blood plasma 4.5 times by using purified water not containing lithium ions, 5 μL was weighed, 55 μL of a third reagent prepared as described below was added thereto, and then heated at 37° C. for 10 minutes. With respect to this mixture, the change in absorbance was obtained by measuring an absorbance during 1 minute at a main wavelength of 545 nm and a complementary wavelength of 596 nm by using JCA-BM6050-type automatic biochemistry analyzer (manufactured by JEOL Ltd.). The concentration of lithium ions was measured from a calibration curve prepared in advance.

Preparation of Reagent for Measuring Lithium Ions

A reagent for measuring lithium ions having the following composition was prepared.

| Third reagent | |
|---|---|
| Perfluoro-5,10,15,20-tetraphenyl-21H,23H-porphyrin | 0.05% by mass |
| Dimethyl sulfoxide | 5% by mass |
| Triethanolamine | 2% by mass |
| Polyethylene glycol-t-octylphenyl ether | 2% by mass |
| Sodium dodecyl sulfate | 2% by mass |

A dilution factor [B/(B−A)] of each diluent solution was obtained from a concentration of lithium ions (A) in the diluent solution after a blood sample was diluted, which was obtained as above, and a concentration of lithium ions (B) in the diluent solution before diluting the blood, and therefore an average value of the dilution factors, and CV (%) which is a coefficient of variation of the dilution factor of 10 specimens prepared with respect to each of the collected blood (80 μL, 60 μL, 40 μL, 30 μL, and 20 μL) were obtained. The results are shown in Table 3.

TABLE 3

| Volume of blood collected (μL) | Volume of Diluent Solution-1 (μL) | Dilution factor (average value of 10 times of measurement) | CV of dilution factor (%) (10 times of measurement) | Washing | Number of washing | Note |
|---|---|---|---|---|---|---|
| 80 | 350 | 9.2 | 3.1 | Washing with pure water | 5 | Comparative Level 8 |
| 60 | 350 | 11.2 | 3.7 | Washing with pure water | 5 | Comparative Level 9 |
| 40 | 350 | 18.1 | 6.4 | Washing with pure water | 5 | Comparative Level 10 |
| 30 | 350 | 21.6 | 8.2 | Washing with pure water | 5 | Comparative Level 11 |
| 20 | 350 | 34.0 | 11.8 | Washing with pure water | 5 | Comparative Level 12 |

From the results in Table 2, it can be understood that average values of dilution factors of Comparative Levels 1, 3, 5, 6, and 7 in which washing was insufficient may be different from results of dilution factors shown in Table 3 which were obtained from lithium ions. In addition, it can be understood that each variation in the measurement results of dilution factors became slightly large. On the other hand, average values of the dilution factors of Comparative Levels 2 and 4 and Reference Levels 1, 2, and 3 in which washing was intensified favorably corresponded to the results of the dilution factors shown in Table 3 which were obtained from lithium ions. Furthermore, it can be understood that, in cases in which a volume of blood collected is 50 µL or less and a dilution factor is 14 times or larger, regarding a level of repeatability and reproducibility of a dilution factor, levels of repeatability and reproducibility of dilution factors of Reference Levels 1, 2, and 3, which were obtained from a concentration of sodium ions in blood as shown in Table 2 were very favorable with respect to results in which levels of repeatability and reproducibility of dilution factors shown in Table 3 which were obtained from lithium ions deteriorated.

Example 1

1. Measurement of Alanine Transaminase (ALT) and Aspartate Aminotransferase (AST)

Immediately after collecting the blood from the vein using a syringe in Reference Example 2, a lancet was used for pricking the fingertip of the same patient of the blood collection to allow blood to flow out of the skin of the fingertip, and then the patient used a sponge capable of absorbing liquid of about 20 µL to 40 µL to soak up the blood after the sponge was washed with pure water three times in the same manner as in Reference Example 2 and dried. The sponge which absorbed the blood was immersed into 350 µL of a diluent solution having the same composition as the diluent solution used in Reference Example 2 so that the blood was sufficiently extracted from the sponge to the diluent solution, blood cell components were filtered through a filter, and therefore a diluent solution having blood plasma components of the blood sample was obtained. As the blood test kit used at this time, a kit washed with pure water three times in the same manner as in Reference Example 2 was used. Thereafter, the diluent solution was sealed and transported to another facility capable of the test. Thereafter, the diluent solution was taken out, and when a dilution factor was measured in the same manner as in the measuring method of a dilution factor using sodium ions of the blood in Reference Example 2, a dilution factor was 19.8. Based on this, it was found that a volume of blood collection was slightly more than 30 µL. When concentrations of ALT and AST in this diluted sample was measured using a commercially available measurement kit (Transaminase CII-Test Wako: manufactured by Wako Pure Chemical Industries, Ltd.), with respect to results in which an ALT value and an AST value, which were analyzed on the basis of the dilution factor measured using a concentration of sodium ions in a sample with a volume of blood collected of 30 µL in Reference Example 2, were 18 U/L and 36 U/L, respectively, results corresponding to the above results were obtained, in which an ALT value and an AST value, which were analyzed from the diluent solution obtained by diluting the blood collected using the sponge as described above, were 18 U/L and 36 U/L, respectively. Therefore, the effect of the present invention was confirmed.

Example 2

A concentration of chloride ions was measured by the following method using the diluent solution from which the dilution factor of blood plasma components of the blood sample was measured using sodium ions in Example 1.

Measurement of Concentration of Chloride Ions in Diluent Solution

Chloride ions were measured by using an ion selective electrode (ISE). A biological specimen was allowed to flow between the ion selective electrodes selectively responding to chloride ions, and reference electrodes, and a concentration of chloride ions was calculated from the electromotive force generated between both electrodes.

The result was obtained, in which a dilution factor of the blood plasma components of the blood sample, which was obtained by measurement of a concentration of sodium ions in the diluent solution of the blood plasma, was the same value as a dilution factor obtained from the measurement value of the concentration of chloride ions of the diluent solution, and 102 mmol/L of the average value of the concentration of chloride ions homeostatically present in blood. Based on the result, it was found that the measurement of the dilution factor obtained from the concentration of sodium ions in Example 1 was performed normally, and it was found that the verification of the measurement is possible.

EXPLANATION OF REFERENCES

1: blood separation instrument
2: blood collection container
3: tubular body
4: cap piston
5: sealing lid
6: cap
7: packing
8: screw portion
9: locking portion
10: bottom portion
11: leg portion
12: slit groove
13: diluent solution
14: expanded diameter section
15: thin portion
16: main body portion
18: reduced diameter section
19: protruded locking portion
20: outer flange portion
21: filtration membrane
22: cover
26: knob portion
27: mandrel portion
28: space
29: lower end portion
31: level difference portion
33: upper end portion
34: top portion

What is claimed is:
1. A blood analysis method, comprising:
a step of diluting a collected blood sample with a diluent solution;

a step of determining a dilution factor by using a normal value of a normal component which is homeostatically present in blood, wherein the normal component which is homeostatically present in blood comprises chloride ions; and a step of analyzing a concentration of a target component in the blood sample, wherein the blood analysis method uses a member selected from the group consisting of a first storing instrument for storing a diluent solution, a separation instrument for separating and recovering blood plasma from the blood sample diluted with the diluent solution, a holding instrument for holding the separation instrument, a second storing instrument for storing the recovered blood plasma, and a sealing instrument for keeping the recovered blood plasma that is stored within the second storing instrument, the diluent solution defines an amount of the normal component which is derived from the diluent solution and/or the member and may be contained in the diluent solution, and a volume of the blood sample is 50 µL or less, and a dilution factor of a blood plasma component in the blood sample is 14 times or more.

2. The blood analysis method according to claim 1, wherein an amount of the normal component which is derived from the member and may be contained in the diluent solution is 0.35 mmol/L or less with respect to the diluent solution.

3. The blood analysis method according to claim 1, wherein the normal component which is homeostatically present in blood further comprises at least one kind of another normal component.

4. The blood analysis method according to claim 3, wherein the at least one kind of another normal component is a normal component selected from total protein or albumins.

5. The blood analysis method according to claim 3, further comprising a step of verifying analysis of a concentration of the target component from a dilution factor obtained by using a normal value of the at least one kind of another normal component.

6. The blood analysis method according to claim 1, wherein the diluent solution does not contain the normal component which is homeostatically present in blood.

7. The blood analysis method according to claim 1, wherein the diluent solution is a buffer solution having a buffering action within a pH range of pH 6.5 to pH 8.0.

8. The blood analysis method according to claim 1, wherein the diluent solution contains an amino alcohol compound selected from the group consisting of 2-amino-2-methyl-1-propanol, 2-ethylaminoethanol, N-methyl-D-glucamine, diethanolamine, and triethanolamine, and a buffering agent selected from the group consisting of 2-[4-(2-hydroxyethyl)-1-piperazinyl]ethanesulfonic acid also called HEPES, N-tris(hydroxymethyl)methyl-2-aminoethanesulfonic acid also called TES, 3-morpholinopropanesulfonic acid also called MOPS, and N,N-bis(2-hydroxyethyl)-2-aminoethanesulfonic acid also called BES.

9. A blood test kit used in the blood analysis method according to claim 1, the blood test kit comprising:

a first storing instrument for storing a diluent solution;

a separation instrument for separating and recovering blood plasma from a blood sample diluted with the diluent solution;

a holding instrument for holding the separation instrument;

a second storing instrument for storing the recovered blood plasma; and a sealing instrument for keeping the recovered blood plasma that is stored within the second storing instrument.

* * * * *